United States Patent
Monfre et al.

(10) Patent No.: US 7,505,801 B2
(45) Date of Patent: Mar. 17, 2009

(54) APPARATUS AND METHOD FOR EASING USE OF A SPECTROPHOTOMETRIC BASED NONINVASIVE ANALYZER

(75) Inventors: Stephen L. Monfre, Gilbert, AZ (US);
George M. Acosta, Menifee, CA (US);
Thomas B. Blank, Gilbert, AZ (US);
Kevin H. Hazen, Gilbert, AZ (US)

(73) Assignee: Sensys Medical, Inc., Chandler, AZ (US)

( * ) Notice: Subject to any disclaimer, the term of this patent is extended or adjusted under 35 U.S.C. 154(b) by 0 days.

(21) Appl. No.: 11/848,139

(22) Filed: Aug. 30, 2007

(65) Prior Publication Data

US 2007/0293743 A1 Dec. 20, 2007

Related U.S. Application Data

(63) Continuation of application No. 10/824,459, filed on Apr. 13, 2004, now Pat. No. 7,333,843.

(60) Provisional application No. 60/463,616, filed on Apr. 16, 2003.

(51) Int. Cl.
*A61B 5/1455* (2006.01)

(52) U.S. Cl. .................. 600/344; 600/316

(58) Field of Classification Search ............... 600/309, 600/316, 322, 344
See application file for complete search history.

(56) References Cited

U.S. PATENT DOCUMENTS

| | | | |
|---|---|---|---|
| 5,596,987 A | 1/1997 | Chance | |
| 5,879,373 A | 3/1999 | Roper et al. | |
| 6,152,876 A * | 11/2000 | Robinson et al. | 600/322 |
| 6,445,939 B1 * | 9/2002 | Swanson et al. | 600/342 |
| 2002/0055671 A1 | 5/2002 | Wu et al. | |

* cited by examiner

*Primary Examiner*—Eric F Winakur
*Assistant Examiner*—Etsub D Berhanu
(74) *Attorney, Agent, or Firm*—Michael A. Glenn; Glenn Patent Group

(57) ABSTRACT

A placement guide apparatus with an improved hydration inducing plug used in coupling a noninvasive analyzer to a sampling site to determine analyte in the human body is disclosed. The hydration inducing plug includes at least one fluoropolymer that may be used as a coupling agent. The guide apparatus may further include an automated or semi-automated coupling fluid delivery system. Use of either of these couplers mitigates issues associated with related technology and enhances noninvasive analyte measurements, such as a near-IR diffuse reflectance based noninvasive glucose concentration analyzer.

8 Claims, 4 Drawing Sheets

APPARATUS AND METHOD FOR EASING USE OF A SPECTROPHOTOMETRIC BASED NONINVASIVE ANALYZER

CROSS REFERENCE TO RELATED APPLICATIONS

This application is a continuation of U.S. patent application Ser. No. 10/824,459, filed Apr. 13, 2004 now U.S. Pat. No.7,333,843, which claims benefits to the U.S. provisional patent application Ser. No. 60/463,616 filed on 16 Apr. 2003, the contents of each of which are incorporated herein in their entirety by this reference thereto.

BACKGROUND OF THE INVENTION

1. Field of the Invention

The invention relates generally to the technology of noninvasive analyte determination in the human body. More particularly, the invention relates to the use of a placement guide in conjunction with a diffuse reflectance based near-IR glucose analyzer. The placement guide couples to a glucose analyzer and has at least one of a hydration inducer and a reservoir for a coupling agent used for automatic or manual delivery of the coupling agent to the sampling site.

2. Description of Related Art

Spectroscopy based noninvasive analyzers deliver external energy in the form of light or rays to a specific sampling site or region of the human body where the photons interact with the chemistry and physiology of the sampled tissue. A portion of the incident photons are scattered or transmitted out of the body where they are detected. Based upon knowledge of the incident photons and detected photons, the chemical and/or structural basis of the sampled site may be deduced. Several distinct advantages to a noninvasive system are the analyses of chemical and structural constituents in the body without the generation of a biohazard in a pain free manner with limited consumables. The technique may also allow for multiple analytes or structural features to be determined at one time. Some common examples of noninvasive analyzers are magnetic resonance imaging (MRI), X-rays, pulse oximeters, and noninvasive glucose analyzers. With the exception of X-rays, these determinations are performed with relatively harmless wavelengths of radiation. Examples herein focus on noninvasive glucose determination, but the principles apply to other modes of noninvasive analyses.

Diabetes

Diabetes is a chronic disease that results in improper production and utilization of insulin, a hormone that facilitates glucose uptake into cells. While a precise cause of diabetes is unknown, genetic factors, environmental factors, and obesity appear to play roles. Diabetics have increased risk in three broad categories: cardiovascular heart disease, retinopathy, and neuropathy. Diabetics may have one or more of the following complications: heart disease and stroke, high blood pressure, kidney disease, neuropathy (nerve disease and amputations), retinopathy, diabetic ketoacidosis, skin conditions, gum disease, impotence, and fetal complications. Diabetes is a leading cause of death and disability worldwide. Moreover, diabetes is merely one among a group of disorders of glucose metabolism that also includes impaired glucose tolerance, and hyperinsulinemia, or hypoglycemia.

Diabetes Prevalence and Trends

Diabetes is an ever more common disease. The World Health Organization (WHO) estimates that diabetes currently afflicts 154 million people worldwide. There are 54 million people with diabetes living in developed countries. The WHO estimates that the number of people with diabetes will grow to 300 million by the year 2025. In the United States, 15.7 million people or 5.9 percent of the population are estimated to have diabetes. Within the United States, the prevalence of adults diagnosed with diabetes increased by 6% in 1999 and rose by 33% between 1990 and 1998. This corresponds to approximately eight hundred thousand new cases every year in America. The estimated total cost to the United States economy alone exceeds $90 billion per year. *Diabetes Statistics*, National Institutes of Health, Publication No. 98-3926, Bethesda, MD. (Nov. 1997).

Long-term clinical studies show that the onset of complications can be significantly reduced through proper control of blood glucose levels. The Diabetes Control and Complications Trial Research Group, *The effect of intensive treatment of diabetes on the development and progression of long-term complications in insulin-dependent diabetes mellitus*, N Eng J of Med, 329:977-86 (1993); U.K. Prospective Diabetes Study (UKPDS) Group, *Intensive blood-glucose control with sulphonylureas or insulin compared with conventional treatment and risk of complications in patients with type 2 diabetes*, Lancet, 352:837-853 (1998); and Y. Ohkubo, H. Kishikawa, E. Araki, T. Miyata, S. Isami, S. Motoyoshi, Y. Kojima, N. Furuyoshi, M. Shichizi, *Intensive insulin therapy prevents the progression of diabetic microvascular complications in Japanese patients with non-insulin-dependent diabetes mellitus: a randomized prospective 6-year study*, Diabetes Res Clin Pract, 28:103-117 (1995).

A vital element of diabetes management is the self-monitoring of blood glucose levels by diabetics in the home environment. However, current monitoring techniques discourage regular use due to the inconvenient and painful nature of drawing blood through the skin prior to analysis. The Diabetes Control and Complication Trial Research Group, supra. As a result, noninvasive measurement of glucose has been identified as a beneficial development for the management of diabetes. Implantable glucose analyzers eventually coupled to an insulin delivery system providing an artificial pancreas are also being pursued.

Sampling Methodology

A wide range of technologies serve to analyze the chemical make-up of the body. These techniques may be broadly categorized into two groups, invasive and noninvasive. For the purposes of this document, a technology that acquires any biosample from the body for analysis or if any part of the measuring apparatus penetrates into the body, the technology is referred to as invasive.

Invasive: Some examples of invasive technologies for glucose determination in the body are those that analyze the biosamples of whole blood, serum, plasma, interstitial fluid, and mixtures or selectively sampled components of the aforementioned. Typically, these samples are analyzed with electrochemical, electroenzymatic, and/or colorimetric approaches. For example, enzymatic and calorimetric approaches may be used to determine the glucose concentration in interstitial fluid samples.

Noninvasive: A number of approaches for determining the glucose concentration in biosamples, have been developed that utilize spectrophotometric technologies. These techniques include: Raman and fluorescence, as well as techniques using light from the ultraviolet through the infrared [ultraviolet (200 to 400 nm), visible (400 to 700 nm), near-IR (700 to 2500 nm or 14,286 to 4000 $cm^{-1}$), and infrared (2500 to 14,285 nm or 4000 to 700 $cm^{-1}$)].

Noninvasive Glucose Determination

There exist a number of noninvasive approaches for glucose determination. These approaches vary widely, but have at least two common steps. First, an apparatus is utilized to acquire a signal from the body without obtaining a biological sample. Second, an algorithm is utilized to convert this signal into a glucose determination.

One type of noninvasive glucose determination is based upon spectra. Typically, a noninvasive apparatus utilizes some form of spectroscopy to acquire the signal or spectrum from the body. Utilized spectroscopic techniques include, but are not limited to: Raman and fluorescence, as well as techniques using light from ultraviolet through the infrared [ultraviolet (200 to 400 nm), visible (400 to 700 nm), near-IR (700 to 2500 nm or 14,286 to 4000 $cm^{-1}$), and infrared (2500 to 14,285 nm or 4000 to 700 $cm^{-1}$)]. A particular range for noninvasive glucose determination in diffuse reflectance mode is about 1100 to 2500 nm or ranges therein. K. Hazen, *Glucose Determination in Biological Matrices Using Near-infrared Spectroscopy*, doctoral dissertation, University of Iowa (1995). It is important to note that these techniques are distinct from the traditional invasive and alternative invasive techniques listed above in that the interrogated sample is a portion of the human body in-situ, not a biological sample acquired from the human body.

Typically, three modes are utilized to collect noninvasive scans: transmittance, transflectance, and/or diffuse reflectance. For example the signal collected, typically being light or a spectrum, may be transmitting through a region of the body such as a fingertip, diffusely reflected, or transflected. Transflected here refers to collection of the signal not at the incident point or area (diffuse reflectance), and not at the opposite side of the sample (transmittance), but rather at some point on the body between the transmitted and diffuse reflectance collection area. For example, transflected light enters the fingertip or forearm in one region and exits in another region typically 0.2 to 5 mm or more away depending on the wavelength utilized. Thus, light that is strongly absorbed by the body such as light near water absorbance maxima at 1450 or 1950 nm would need to be collected after a small radial divergence and light that is less absorbed such as light near water absorbance minima at 1300, 1600, or 2250 nm may be collected at greater radial or transflected distances from the incident photons.

Noninvasive techniques are not limited to using the fingertip as a measurement site. Alternative sites for taking noninvasive measurements include: a hand, finger, palmar region, base of thumb, wrist, dorsal aspect of the wrist, forearm, volar aspect of the forearm, dorsal aspect of the forearm, upper arm, head, earlobe, eye, tongue, chest, torso, abdominal region, thigh, calf, foot, plantar region, and toe. It is important to note that noninvasive techniques do not have to be based upon spectroscopy. For example, a bioimpedence meter would be considered a noninvasive device. Within the context of the invention, any device that reads a signal from the body without penetrating the skin and collecting a biological sample is referred to as a noninvasive glucose analyzer. For example, a bioimpedence meter is a noninvasive device.

Calibration

Glucose analyzers require calibration. This is true for all types of glucose analyzers such as traditional invasive, alternative invasive, noninvasive, and implantable analyzers. One fact associated with noninvasive glucose analyzers is that they are secondary in nature, that is, they do not measure blood glucose levels directly. This means that a primary method is required to calibrate these devices to measure blood glucose levels properly. Many methods of calibration exist.

One noninvasive technology, near-infrared spectroscopy, requires that a mathematical relationship between an in vivo near-infrared measurement and the actual blood glucose value be developed. This is achieved through the collection of in-vivo NIR measurements with corresponding blood glucose values that have been obtained directly through the use of measurement tools like a HEMOCUE or a YSI (YSI INCORPORATED, Yellow Springs Ohio), or any appropriate and accurate traditional invasive reference device.

For spectrophotometric based analyzers, there are several univariate and multivariate methods that may be utilized to develop the mathematical relationship between the measured signal and the actual blood glucose value. However, the basic equation being solved is known as the Beer-Lambert Law. This law states that the strength of an absorbance/reflectance measurement is proportional to the concentration of the analyte which is being measured, as in equation 1, $$A = \epsilon b C \tag{1}$$

where A is the absorbance/reflectance measurement at a given wavelength of light, $\epsilon$ is the molar absorptivity associated with the molecule of interest at the same given wavelength, b is the distance that the light travels, and C is the concentration of the molecule of interest (glucose).

Chemometric calibration techniques extract the glucose signal from the measured spectrum through various methods of signal processing and calibration including one or more mathematical models. The models are developed through the process of calibration on the basis of an exemplary set of spectral measurements known as the calibration set and associated set of reference blood glucose concentrations based upon an analysis of capillary blood or venous blood. Common multivariate approaches requiring an exemplary reference glucose concentration vector for each sample spectrum in a calibration include partial least squares (PLS) and principal component regression (PCR). Many additional forms of calibration are known, such as neural networks.

There are a number of reports on noninvasive glucose technologies. Some of these relate to general instrumentation configurations required for noninvasive glucose determination. Others refer to sampling technologies. Those most related to the present invention are briefly reviewed here:

As outlined above, there have been a number of studies documenting the need for an accurate and precise noninvasive glucose analyzer.

R. Barnes, J. Brasch, D. Purdy, W. Lougheed, Non-invasive determination of analyte concentration in body of mammals, U.S. Pat. No. 5,379,764 (Jan. 10, 1995) describe a noninvasive glucose analyzer that utilizes data pretreatment in conjunction with a multivariate analysis to determine blood glucose concentrations.

General Instrumentation:

P. Rolfe, Investigating substances in a patient's bloodstream, UK Patent Application No. 2,033,575 (Aug. 24, 1979) describe an apparatus for directing light into the body, detecting attenuated backscattered light, and utilizing the collected signal to determine glucose concentrations in or near the bloodstream.

C. Dahne, D. Gross, Spectrophotometric method and apparatus for the non-invasive, U.S. Pat. No. 4,655,225 (Apr. 7, 1987) describe a method and apparatus for directing light into a patient's body, collecting transmitted or backscattered light, and determining glucose from selected near-IR wavelength bands. Wavelengths include 1560 to 1590, 1750 to 1780, 2085 to 2115, and 2255 to 2285 nm with at least one additional reference signal from 1000 to 2700 nm.

M. Robinson, K. Ward, R. Eaton, D. Haaland, Method and apparatus for determining the similarity of a biological analyte from a model constructed from known biological fluids, U.S. Pat. No. 4,975,581 (Dec. 4, 1990) describe a method and apparatus for measuring a concentration of a biological analyte such as glucose using infrared spectroscopy in conjunction with a multivariate model. The multivariate model is constructed form plural known biological fluid samples.

J. Hall, T. Cadell, Method and device for measuring concentration levels of blood constituents non-invasively, U.S. Pat. No. 5,361,758 (Nov. 8, 1994) describe a noninvasive device and method for determining analyte concentrations within a living subject utilizing polychromatic light, a wavelength separation device, and an array detector. The apparatus utilizes a receptor shaped to accept a fingertip with means for blocking extraneous light.

S. Malin, G Khalil, Method and apparatus for multi-spectral analysis of organic blood analytes in noninvasive infrared spectroscopy, U.S. Pat. No. 6,040,578 Mar. 21, 2000) describe a method and apparatus for determination of an organic blood analyte using multi-spectral analysis in the near-IR. A plurality distinct nonoverlapping regions of wavelengths are incident upon a sample surface, diffusely reflected radiation is collected, and the analyte concentration is determined via chemometric techniques.

Specular Reflectance:

R. Messerschmidt, D Sting Blocker device for eliminating specular reflectance from a diffuse reflectance spectrum, U.S. Pat. No. 4,661,706 (Apr. 28, 1987) describe a reduction of specular reflectance by a mechanical device. A blade-like device "skims" the specular light before it can impinge on the detector. A disadvantage of this system is that it does not efficiently collect diffusely reflected light and the alignment is problematic.

R. Messerschmidt, M. Robinson Diffuse reflectance monitoring apparatus, U.S. Pat. No. 5,636,633 (Jun. 10, 1997) describe a specular control device for diffuse reflectance spectroscopy utilizing a group of reflecting and open sections.

R. Messerschmidt, M. Robinson Diffuse reflectance monitoring apparatus, U.S. Pat. No. 5,935,062 (Aug. 10, 1999) and R. Messerschmidt, M. Robinson Diffuse reflectance monitoring apparatus, U.S. Pat. No. 6,230,034 (May 8, 2001) describe a diffuse reflectance control device that can discriminate between diffusely reflected light that is reflected from selected depths. This control device may additionally act as a blocker to prevent specularly reflected light from reaching the detector.

Malin et. al., supra describe the utilization of specularly reflected light in regions of high water absorbance such as 1450 and 1900 nm to mark the presence of outlier spectra wherein the specularly reflected light is not sufficiently reduced.

K. Hazen, G. Acosta, A. Abul-Haj, R. Abul-Haj, Apparatus and method for reproducibly modifying localized absorption and scattering coefficients at a tissue measurement site during optical sampling, U.S. Pat. No. 6,534,012 (Mar. 18, 2003) describe a mechanical device for applying sufficient and reproducible contact of the apparatus to the sampling medium to minimize specular reflectance. Further the apparatus allows for reproducible applied pressure to the sampling site and reproducible temperature at the sampling site.

Temperature:

It is well known that many physiological constituents have near-IR absorbance spectra that are sensitive in terms of magnitude and location to localized temperature. This has been reported as impacting noninvasive glucose determinations. Hazen, et. al., supra.

Coupling Fluid:

Index of fraction matching between the sampling apparatus and sampled medium is well known. Glycerol is a common index matching fluid for optics to skin. A number of patents disclose more specific coupling fluids with important sampling parameters.

R. Messerschmidt, Method for non-invasive blood analyte measurement with improved optical interface, U.S. Pat. No. 5,655,530 (Aug. 12, 1997), and R. Messerschmidt Method for non-invasive blood analyte measurement with improved optical interface, U.S. Pat. No. 5,823,951 describe an index-matching medium for use between a sensor probe and the skin surface. The index-matching medium is a composition containing perfluorocarbons and chlorofluorocarbons.

M. Robinson, R. Messerschmidt, Method for non-invasive blood analyte measurement with improved optical interface, U.S. Pat. No. 6,152,876 (Nov. 28, 2000) and M. Rohrscheib, C. Gardner, M. Robinson, Method and apparatus for non-invasive blood analyte measurement with fluid compartment equilibration, U.S. Pat. No. 6,240,306 (May 29, 2001) describe an index-matching medium to improve the interface between the sensor probe and skin surface during spectroscopic analysis. The index-matching medium is preferably a composition containing chlorofluorocarbons. The composition can also contain perfluorocarbons.

T. Blank, G. Acosta, M. Mattu, S. Monfre, Fiber optic probe guide placement guide, U.S. Pat. No. 6,415,167 (Jul. 2, 2002) describe a coupling fluid of one or more perfluoro compounds where a quantity of the coupling fluid is placed at an interface of the optical probe and measurement site. Notably, perfluoro compounds do not have the toxicity associated with chlorofluorocarbons.

Guide:

Blank et. al., supra describe the utilization of a guide in conjunction with a noninvasive glucose analyzer in order to increase precision of the location of the sampled site resulting in increased accuracy and precision in a noninvasive glucose determination.

In all of the related technology of this section, no suggestion of automated analysis is made. Further, no suggestion is made for a fluoropolymer hydration inducer or for a coupling fluid reservoir within the guide. Both of these guide features ease the use of a bioanalyzer such as a near-IR based noninvasive glucose analyzer. In addition, to date no FDA device has been approved for the utilization by an individual or a medical professional for noninvasive glucose concentration determination.

The Problem

Noninvasive glucose analyzers reported to date generally require precision in sampling in order to accurately determine glucose concentrations in the body. The measurement is complicated by every manual step required in the spectral acquisition process utilized in a given glucose determination. Complications include any of a requirement of time, a step requiring manual dexterity, or movement of measurement apparatus that may be bulky, fragile, or sensitive in terms of returned analytical signal. Elimination or automation of steps required for a noninvasive glucose determination is beneficial for at least one of increasing marketability of the analyzer, increasing the number of people who may utilize the analyzer, reduction in time requirements associated with a glucose determination, and increased precision and/or accuracy of a glucose determination. Specifically, preparation of the sampling site in terms of temperature, historesis of applied pressure, hydration, and optical scattering parameters involving actions from the user that may be any of technically challenging, time consuming, and error inducing.

What is desired is a mechanism for reducing user input through methods and apparatus such as a hydration inducer and a coupling agent enhancement integrated into a guide used in conjunction with a noninvasive glucose analyzer.

SUMMARY OF THE INVENTION

A placement guide apparatus and method for use in conjunction with an optically based noninvasive glucose analyzer is disclosed. Two coupling agents are incorporated into the guide. The first is a hydration inducing plug used for optical coupling of the measurement apparatus to the sampling site. The second is a fluorocarbon mixture used for optical coupling of the measurement apparatus to the sampling site.

The guide has a mount, an aperture defined by the mount, and an optical coupling apparatus, namely a hydration inducing plug. The mount has a contact surface at one end, at least a portion of the contact surface being contact with a sampling site. The aperture is adapted to receive an optical probe, which is part of the optically based noninvasive analyzer. The hydration inducing plug is securely attached, from the aperture, to the mount at the contacting end. The outer surface of the hydration inducing plug is aligned with the mount's contact surface and is in direct contact with the sampling site. When the optical probe is coupled into the aperture, the hydration inducing plug acts an optical interface between the optical probe and the sampling site. The hydration inducing plug is made of a material or materials, such as fluoropolymer, having properties that include at least one of being near-IR transmissive, hydrophobic, refractive index matching, and insulating.

In one embodiment, the hydration inducing plug is an evenly flat member, the edge of which is securely attached to the mount of the guide. When the optical probe is coupled with the guide, both the incidental optics and the collection optics are in direct contact with the inner surface of the hydration inducing plug.

In another embodiment, the hydration inducing plug includes multiple layers. Each of the layers may have its own physical properties. The multiple layers may be evenly or unevenly heat compressed. In an uneven heat compression case, the central area of the plug is made thinner than the surrounding area.

In another embodiment, there is a hole in the center of the hydration inducing plug, so that when the optical probe is coupled with the guide, the collection optics of the optical probe is fittingly coupled into the hole and has direct contact with the sampling site, while the incident optics of the optical probe maintains direct contact with the surrounding area of the hydration inducing plug. To increase detection, the hydration inducing plug may be shaped as an optical convexity. In that case, the incident photons travel in the air for a short distance before they reach the inner surface of the plug.

Yet in another embodiment, the guide contains one or more reservoirs for containment of an optical coupling fluid that may be near-IR inactive. A guide incorporating at least one of these couplers allows for increased ease of use and increased in precision and accuracy of near-IR based noninvasive glucose determinations. The modified guide allows for automated, semi-automated, or simplified sampling associated with a near-IR based noninvasive glucose analyzer or for separate optical analyses that use a guide.

The hydration inducing plug, also called hydration inducer coupler, replaces an older plug that has to be manually removed between samples. The removal and replacement after sampling of the plug results in several issues such as: (1) time involved; (2) manually dexterity; (3) introduction of pressure transients; (4) introduction of temperature transients; (5) possibility of loss of removable item; and (6) possibility of introducing contaminants to the sampling site. The hydration inducing plug according to the invention mitigates all of these issues.

The guide coupling fluid reservoir simplifies application of a coupling fluid. To date, application of coupling fluid to a measurement site has been achieved by manually placing an externally stored fluid onto the sampling site. There are many issues related to this including: (1) time involved; (2) manual dexterity requirements; (3) external storage space required; (4) portability concerns such as carrying the coupling fluid for use with a portable analyzer; (5) introduction of pressure transients, such as bumping the sampling site when applying the coupling fluid; and (6) introduction of temperature transients, such as applying a cold coupling fluid to the sampling site. The coupling fluid reservoir scheme according to the invention allows for automated, semi-automated, or simplified coupling fluid application that mitigates all of these issues.

DETAILED DESCRIPTION OF THE INVENTION

Figure 1A:
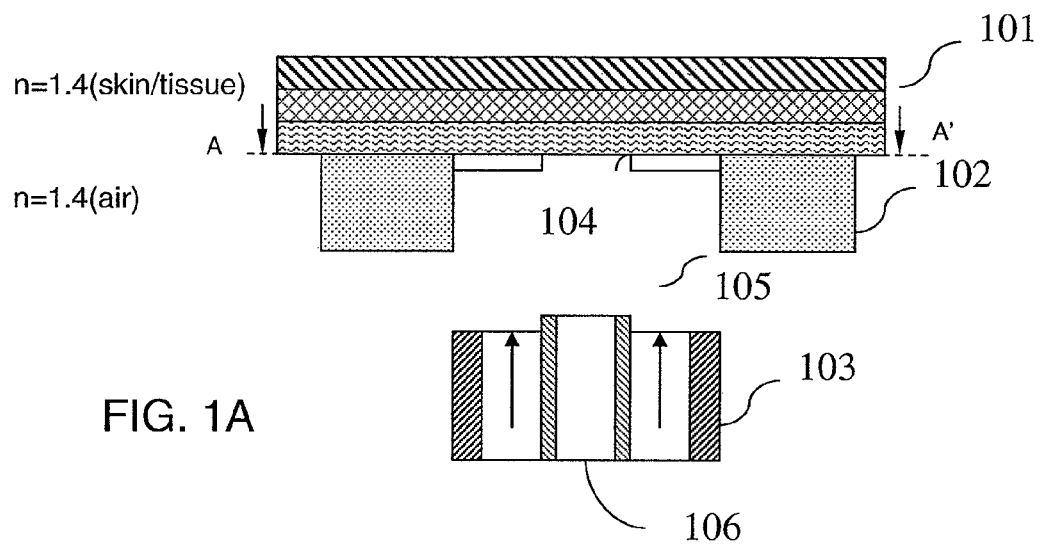
FIG. 1A is a schematic diagram showing the front, cross-sectional view of a piece of sampling skin, a placement guide in contact with the sampling skin, and an optical probe which has not been coupled with the guide according to the invention.

FIG. 1A is a schematic diagram showing the front, cross-sectional view of a piece of sampling skin, a placement guide in contact with the sampling skin, and an optical probe which has not yet been coupled with the guide according to one embodiment of the invention. In FIG. 1A, skin 101 is schematically represented in layers. These layers include the stratum corneum, epidermis, dermis, and adipose tissue, as well as underlying structures, such as muscle. Each of these layers includes many sub-layers and structures. The guide includes a mount 102, also called a guide lock, that is semi-permanently attached to a skin surface. The mount 102 may be in any shape, such as substantially rectangular, circular, oval, and polygonal. The guide includes an aperture which is defined by the mount 102. The aperture may be in any shape, such as substantially rectangular, circular, oval, triangular, hexagonal, and polygonal. The guide may be attached for one or more subsequent glucose determinations and is typically attached to the skin for the period of a waking day. The guide may be attached for longer periods of time such as days or weeks or for shorter periods of time such as about four or eight hours. The guide may be viewed as one-half of a lock and key mechanism where the key aspect of the mechanism is the associated part on the glucose analyzer, i.e. the optic probe that couples to the guide 103. The key may be a fiber optic, a bundle of fibers, or open air optics as described in the co-pending U.S. patent application Ser. No. 10/349,573. Additional disclosure on the guide is provided in Blank, et. al., supra and in the co-pending U.S. patent application Ser. No. 10/170,921, which is incorporated herein in their entirety by this reference thereto.

The guide may be attached to the skin surface as in Blank, et. al., supra and as in the co-pending T. Blank, G. Acosta, M. Mattu, M. Makarewicz, S. Monfre, A. Lorenz, T. Ruchti, Optical sampling interface for in-vivo measurement of tissue, U.S. patent application Ser. No. 10/170,921 (filed Jun. 12, 2002). Typically a thin film double sided adhesive is used to couple the guide to the sampling site with a hole punched into the adhesive that correlates in position to the sample site actually probed by photons collected by the glucose analyzer. The adhesive may be a moleskin adhesive layer. The adhesive may be used to help contain the coupling fluid as discussed below.

In the embodiment pictured in FIG. 1A, the guide has an additional component that fits between the skin surface and the sampling optical probe 103. This added component is the coupling member, which is referred herein after as hydration inducing plug 104, although it may be referred to alternatively as a plug, coupler, hydration inducer, or index matching element or structure. The hydration inducing plug 104 is here used in conjunction with a noninvasive glucose analyzer for at least one of: (1) enhancement of hydration of the sampling site; (2) temperature control and/or stabilization of the sampling site; (3) optical coupling of the glucose analyzer to the sampling site; and (4) minimization of collected specular reflectance.

The hydration inducing plug 104 serves many of the same purposes as a previously described separate element, herein referred to as the old plug or traditional plug. The old plug was first introduced in Blank, et. al., supra. The old plug basically serves as a hydration inducer or accelerator and is made of polycarbonate. As mentioned above the old plug has many potential issues, such as requiring time and ability from the user and introducing the risk of error introduction in the sampling process through parameters, such as introduction of temperature and pressure transients at the sampling site.

The use of the hydration inducing plug 104 that is attached to the guide and that does not need to be removed and replaced between samples has multiple advantages. First, as the hydration inducing plug 104 is always present, it may not be lost. Second, it acts as a natural barrier to contaminants reaching the sample site. Third, it is maintained at skin temperature by the body and does not introduce a temperature transient at the sample site as a removed plug that become cold would do when replaced at the sampling site. Fourth, since the hydration inducing plug 104 is flexible and does not need to be replaced, the risks of pressure transients associated with replacing the older plug in contact with the sampling site are mitigated. Fifth, as the hydration inducing plug 104 is passive it does not require time to remove and replace nor does it require manual dexterity to do so. Sixth, external storage of a fluid and applicator devices is not required.

Figure 1B:
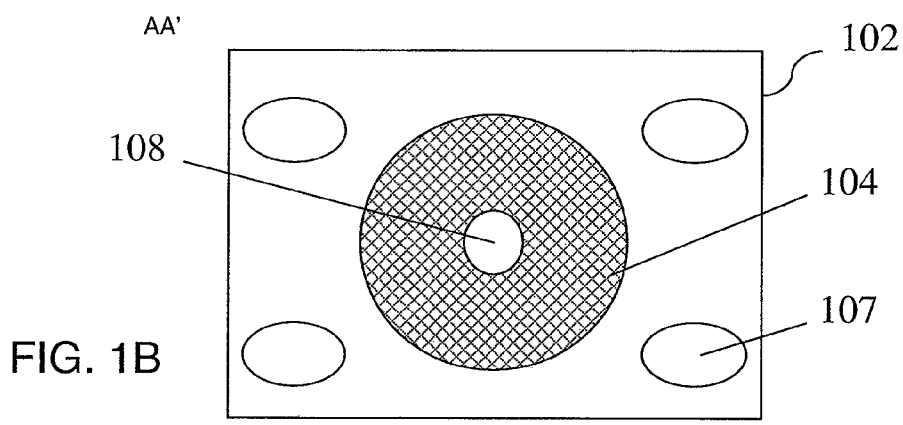
FIG. 1B is a schematic diagram showing the top view of the guide's mount and the hydration inducing plug according to the invention.

FIG. 1B is a schematic diagram showing the top view of the guide's mount and the hydration inducing plug. The ovals 107 represent optional cut outs on the guide surface that allow for temperature control and/or a lighter guide. Associated pressure and temperature benefits are further described in the co-pending U.S. application Ser. No. 09/954,856.

Figure 1C:
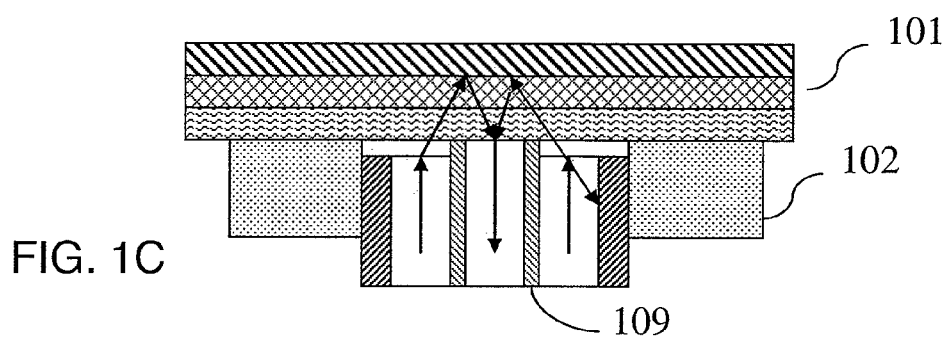
FIG. 1C is a schematic diagram showing the front, cross-sectional view of a piece of sampling skin, a placement guide in contact with the sampling skin, and an optical probe which is coupled with the guide according to the invention.

FIG. 1C is a schematic diagram showing the front, cross-sectional view of a piece of sampling skin, a placement guide in contact with the sampling skin, and an optical probe which is coupled with the guide. In the embodiment presented in FIGS. 1A-1C, the hydration inducing plug 104 has a hole 108 in the center that allows a collection member (optics) 106 of the optic probe 103 to penetrate to the skin surface. The hole 108 is used in order to minimize specular reflectance off of the skin surface when the lock and key mechanism is a single unit. As shown in FIG. 1C, an optional spacer 109 is set between the incident member (optics) 105 and the collection member (optics) 106. The spacer 109 may be used to block specular reflectance but may also be used to sample photons from a larger optical depth. The hole 108 in the center may be created by mechanical or optical means such as a laser punch.

The skin sample 101 is coupled to the glucose analyzer through the guide as pictured in FIG. 1C. The incident photons are delivered into the skin sample 101 through the incident member (optics) 105 and then through the hydration inducing plug 104. The collection member (optics) 106 for collecting returned photons is in direct contact with the skin sample 101. The path of the photons is pictured schematically to enhance understanding of where the photons are traveling in the particular embodiment. Those skilled in the art will appreciate that the actual ray trace of the photons is much more complex than is schematically pictured.

Coupler Properties

In all embodiments within this specification, the desirable properties of the hydration inducing plug 104 include at least one of: (1) hydrophobic; (2) insulating; (3) mechanically flexible and strong; (4) near-IR transmissive from 1100 to 1900 nm; and (5) index of refraction matched.

Some examples of materials that fulfill all of these criteria are fluoropolymers. Fluoropolymers are available in almost any shape and thickness. For example, fluoropolymer films are available from about 25 μm thick to 1 to 3 mm in thickness. Certainly, thicker layers are available. Particular examples of fluoropolymers include Teflon® and Teflon® AF. The term Teflon is used in this specification to represent a fluoropolymer due to the wide recognition of the properties of Teflon, but many additional fluoropolymers have the characteristics described herein.

A fluoropolymer such as Teflon is hydrophobic. As a result, Teflon placed on the surface of the skin results in hydration of the covered skin sample site from the deeper internal layers of skin out towards the surface. The use of a hydrophobic barrier may result in both the increased degree of hydration of the surface structures of the skin and a reduction in the required time to achieve a given hydration level. Both of these are important in the performance of noninvasive glucose analyzers as it results in an increased average depth of penetration of the incident photons due to fewer locations of strong index of refraction differences between dry tissue and air pockets. This results in less scattering and hence deeper average photon penetration. Further, a consistent hydration level results in more precise sampling.

Teflon is a poor thermal conductor. This means that the sampled surface may be insulated from environmental temperature variations. This is important because temperature fluxuations affect the wavelength and magnitude of near-IR absorbance of many skin constituents such as water, protein, and glucose. These changes in optical properties have been reported as detrimental to chemometric procedures, such as mean centering and multivariate analysis such as PCR or PLS, which are commonly applied in near-IR based noninvasive glucose determinations.

Very thin films of Teflon are available or may be prepared that have great flexibility and are strong. This allows the Teflon to couple readily to the sample site without resulting in alterations of the sampling site due to mechanical rigidness. The importance of applying minimal physical perturbations to the sampling site has been outlined in Hazen, et. al. supra and M. Makarewicz, M. Mattu, T. Blank, G. Acosta, E. Handy, W. Hay, T. Stippick, B. Richie, Method and apparatus for minimizing spectral interference due to within and between sample variations, U.S. patent application Ser. No. 09/954,856 (filed Sep. 17, 2001).

Teflon AF is greater than 90% transmissive from 400 to 2000 nm, as reported in http://www.dupont.com/teflon/af/unique.html. This allows incident photons from the sampling probe to penetrate through the hydration inducing plug into the sampling region of the skin. As is obvious to those skilled in the art, the transmittance of the sampling photons through the hydration barrier is critical if the hydration barrier is to be left in the optical path during sampling.

Refractive Index

Teflon AF has a refractive index of around 1.32 at room temperature. The refractive index of Teflon AF has been reported as varying from 1.29 to 1.316 as temperature decreases from 300 to 100° C. according to the documentation in http://www.dupont.com/teflon/af/unique.html. Notably, this is nearly equivalent to the refractive index of fluorocarbons such as Fluorinert and FC-40 that have been reported to be utilized as near-IR coupling agents in noninvasive glucose determination (discussed below). The refractive index and transmission characteristics of Teflon AF result in optical throughput similar to systems that utilize coupling fluids such as FC-40.

In one embodiment of the invention, the optically transparent plug may mitigate or eliminate the need for a coupling fluid. That is, the plug acts as an optical coupler based upon having a refractive index between that of the skin and of the surrounding medium through which the incident photons or collection photons are traveling. For example, 2.8% of normally incident photons traveling from air with a refractive index of 1.0 to skin with a refractive index of 1.4 is reflected. With an intermediate layer, such as Teflon AF, the percentage of reflected photons for the same case reduces to 1.8%. Hence, more photons may penetrate into the sample and the resulting signal to noise may increase. This is exactly one of the purposes of an optical coupling fluid, such as a fluorocarbon molecule like FC-40. In this case, the hydrophobic nature of Teflon results in hydration of the interface between the Teflon and skin. Because water has an index of refraction of 1.33 which is between the 1.30 and 1.4 indices of Teflon AF and skin, this may further increase the percentage of incident photons penetrating into the sample.

Figure 2A:
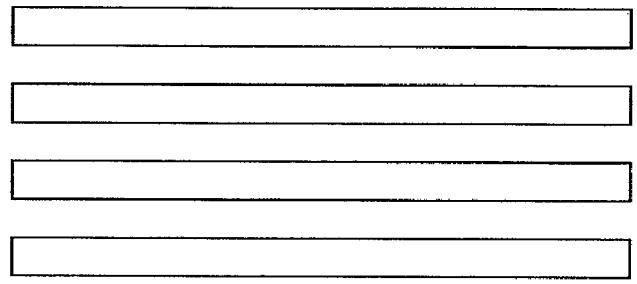
FIGS. 2A-2D are schematic diagrams showing multiple layers being heat compressed together used for the hydration inducing plug according to the invention.

It is possible to construct the coupler out of more than one layer. Individual film layers of different fluoropolymer sheets are pictured in FIG. 2A. Two or more layers may be combined. Each layer may have its own physical properties, such as differences in refractive index.

Figure 2B:
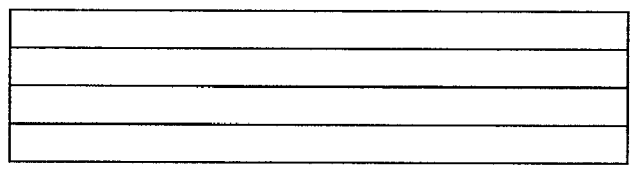

As shown in FIG. 2B, several sheets are pressed together to remove air gaps into a composite film or composite sheet. Combining the layers in a partial vacuum can reduce trapped air bubbles, which is important when trying to match the indices of refraction. Arranging two or more sheets of the plastic or polymer in order of increasing or decreasing refractive index allows a composite material to be formed that has enhanced optical coupling abilities. For example, normal incident photons moving from air with an index of refraction of 1.0 to skin with an index of refraction of 1.4 results in 97.2% of the photons entering the skin, not accounting form surface irregularities. An intermediate coupling layer with an index of refraction of 1.30 increases the light throughput to 98.2%. This means that observed light throughput in the glucose analyzer can be increased by approximately 1% using a Teflon AF layer with an index of refraction of 1.30 between the air and the skin. Additional layers may further increase light throughput as shown in Table 1. This is calculated using the Fresnel equation.

TABLE 1

Light throughput from air to skin based upon index of refraction.

| Indices of Refraction Layer n/n + 1/etc . . . | Light Throughput (Percent) |
| --- | --- |
| 1.0/1.4 | 97.2 |
| 1.0/1.30/1.4 | 98.2 |
| 1.0/1.20/1.30/1.4 | 98.9 |
| 1.0/1.1/1.2/1.3/1.4 | 99.3 |

Figure 2C:
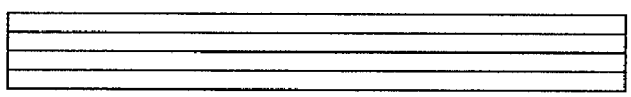

In FIG. 2C, the sheets of FIG. 2B are heat seated together to form a thinner film than that presented in FIG. 2B. The resulting film may have mechanical advantages, such as a thinner thickness and strength. In addition, the refractive index of the compressed film is different than the uncompressed film. For example, layer 1 with an index of refraction of $n_1$ may have a new index of refraction $n_1$ as shown in FIG. 1C after heating forming. Particularly, the index of refraction of the independent layers may be higher than those of the original layers. In addition, the reaching of a glass transition temperature can form intermediate layers with intermediate refractive indices on an atomic scale. The heat seated film of multiple layers may be used when coupled to a sample, such as skin, to increase the light throughput according to the Fresnel equation as demonstrated above and in Table 1.

In the formation of the sheets, a press may be used. The press may be heated. To reduce formation of air bubbles between layers, the press may be under a vacuum. The press may be optically smooth to increase light throughput of normally incident radiation. Similarly, the press may be optically rough if diffuse light is preferred. This may be useful for the application of reducing the amount of light propagating through the length and/or width of the sheet as in a light pipe or in reducing specular reflectance. The press may be the outer dimensions of an optic. This would allow the layers to be pressed into a light directing optic. Finally, the varying thickness would allow incident light to be wavelength separated. That is, as light is passed through the material, it would be wavelength separated by refraction.

Figure 2D:
Figure 3A:
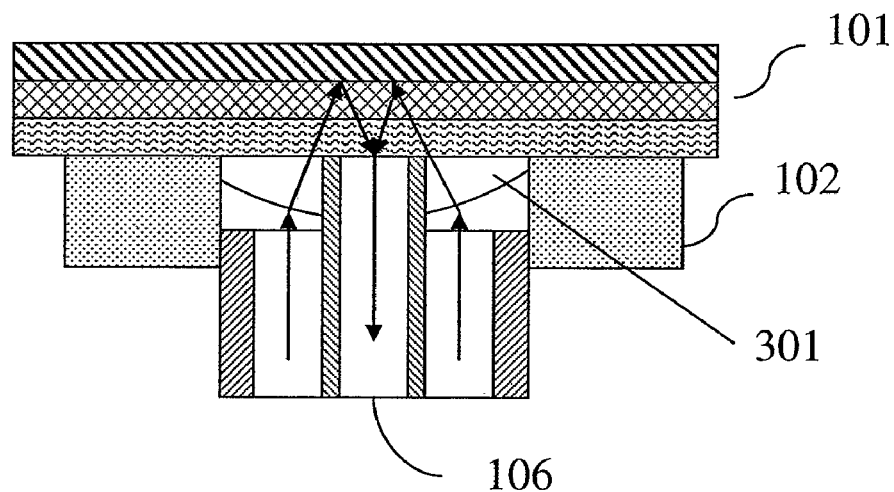
FIG. 3A is a schematic diagram showing the front, cross-sectional view of a piece of sampling skin, a placement guide with a convex hydration inducing plug, and an optical probe which is coupled with the guide according to the invention.

In FIG. 2D, different areas of the sheets of FIG. 2B are compressed or heat seated to varying degrees. For example, the central point of the coupler may be heat compressed to form a thinner layer. This layer may be the region coupling the skin to the collection fiber of FIG. 3C. The benefits of this are discussed below.

The stacked layers of fluoropolymer sheets discussed above may be coupled to a number of other substrates and used to increase incident light throughput. For example, the fluoropolymer films may be attached to filters, longpass filter, shortpass filter, bandpass optics, lenses, optics, and/or fiber optics and used as a cheap method of anti-reflection coating.

Configurations

In another embodiment, the hydration inducing plug may be shaped into a light directing optic. This is presented schematically in FIG. 3A. Here, incident photons are traveling through air when they reach the hydration inducing plug 301 which has a convex inner surface. The inducing plug 301 is shaped so as to direct light towards the central collecting optic(s) 106. This may have the effect of increasing light detection from a central light collection optic, such as a fiber or a light pipe. With appropriate shape to the optic in conjunction with the rest of the optical system, the average depth of penetration of the photons may be adjusted. As described below, the guide as a whole may be a disposable item, or be an item that is periodically removed and replaced. If the algorithm treats acquired spectra in a fashion that incorporates a bias correction, the precision of the optic would not have to be held to high standards. That is, the light throughput could be adjusted for each individual guide by subtracting the average photon flux through guide.

Figure 3B:
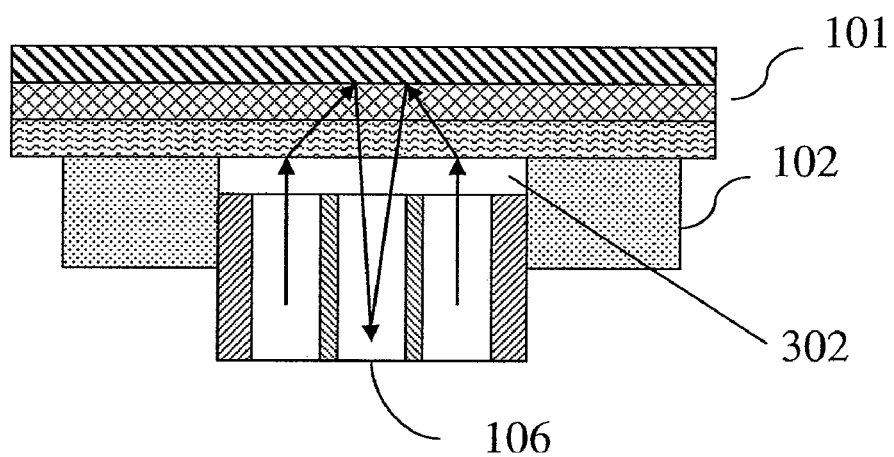
FIG. 3B is a schematic diagram showing the front, cross-sectional view of a piece of sampling skin, a placement guide with an evenly flat hydration inducing plug, and an optical probe which is coupled with the guide according to the invention.
Figure 3C:
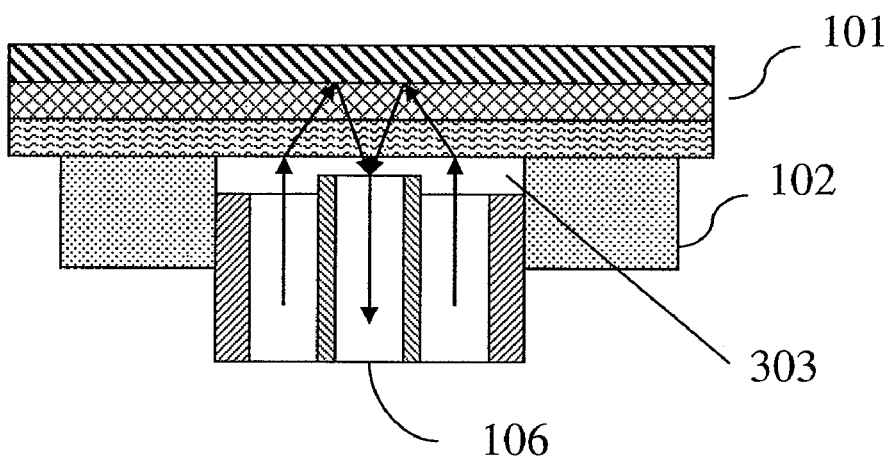
FIG. 3C is a schematic diagram showing the front, cross-sectional view of a piece of sampling skin, a placement guide with a concave hydration inducing plug, and an optical probe which is coupled with the guide according to the invention.

In another embodiment, as shown in FIG. 3B, the hydration inducing plug 302 covers the entire sampling site so that both incident photons onto the skin and photons emerging from the skin must penetrate through the layer. This configuration has a risk of allowing the detection of specularly reflected light. That is collection of light that has not penetrated into the sample site but is reflected off of the surface of the skin or is reflected off of layers within the hydration inducing plug 302. It has been demonstrated that detection of significant levels of specularly reflected light may be detrimental to a near-IR based noninvasive glucose analyzer. It is noted that the amount of detected specular reflectance can be reduced by any of more collimated incident radiation, a thinner hydration inducer, a wider spacer, or reduction of the numerical aperture of the collection optic(s). It is obvious to those skilled in the art that the plug thickness and the spacer width coupled with the numerical aperture of the collection optic(s) and incident angle of the photons may be adjusted to minimize the degree of collection of spectrally reflected light.

In another embodiment as shown in FIG. 2D, the hydration inducing plug 303 covers the entire sample site probed by the incident photons, but the central area of plug is thinner than the surrounding area. In other words, the inner surface of the plug is concave toward the sampling skin. For example, if the plug is made of Teflon, the central area correlating with the collection optic(s) 106 may be heated and pressed into a very thin layer. The dimensions of the compressed region may be on the order of 0.001 inch or 25 μm. Combined with a spacer of 10 to 300 μm and the refractive index of a collection fiber with a low numerical aperture fiber such as fused silica, the degree of spectrally reflected light optically coupled into the collection fiber is minimal relative to the degree of collected signal from the sample. The pressed region of the coupler that is in contact with the spacer may be made with a press that is rough to reduce the horizontal light pipe characteristics of the coupler.

Advantages of a Coupler Integrally Coupled to the Guide

Previously, a traditional plug or older plug has been used in the placement guide. The plug has several purposes. First, the plug is utilized to increase hydration of the sampling site. Increases in hydration may initiate in the deeper layers of the outer skin and progress towards the outer layer of the skin. Second, the plug acts as a barrier to foreign objects such as dirt from contaminating the sampling site. Third, the plug acts as an insulator stabilizing the sample site temperature.

In any of the above configurations, a hydration inducing plug of a material such as a fluoropolymer or Teflon, applied over the sampling site has several advantages:

First, the older traditional plug is an object that may be misplaced whereas the hydration inducing plug according to the invention is attached securely to the mount of the guide.

Second, a hydration induced such as a Teflon film is always in contact with the sampling site and/or coupling fluid. This means that the localized pressure is constant. Removing and replacing the traditional plug often results in small localized pressure transients, which may adversely affect the precision of a near-IR based noninvasive glucose analyzer. The importance of applying minimal physical perturbations to the sampling site has been outlined in Hazen, et. al., supra and M. Makarewicz, M. Mattu, T. Blank, G. Acosta, E. Handy, W. Hay, T. Stippick, B. Richie, Method and apparatus for minimizing spectral interference due to within and between sample variations, U.S. patent application Ser. No. 09/954,856 (filed Sep. 17, 2001).

Third, the old plug is a bulky item that is quite thick. The protrusion from the surface of the skin makes it easy to bump or jar. This physical jarring is transferred to the sampling site. As mentioned above, this may be quite detrimental to the noninvasive glucose determination.

Fourth, the old plug has to be physically removed and replaced by the user. This requires time and manual dexterity. As the hydration inducing plug according to the invention is integrally part of the guide, this step becomes unnecessary.

Fifth, while both the traditional plug and the new hydration inducing plug according to the invention act as an insulator, the removal of the plug away from the sampling site allows it to change temperatures. This results in a localized temperature transient when replaced onto the sampling site.

Guide Reservoir Embodiments

Figure 4A:
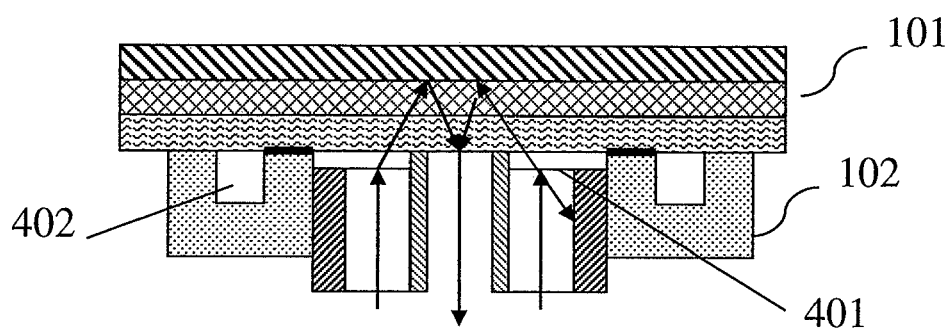
FIG. 4A is a schematic diagram showing the front, cross-sectional view of a piece of sampling skin, a placement guide with a hydration inducing plug and with at least one reservoir in the guide's mount, and an optical probe which is coupled with the guide according to the invention.

The guide may contain one or more cavities or reservoirs in the mount of the guide for containing a coupling agent. FIG. 4A is a schematic diagram showing the front, cross-sectional view of a piece of sampling skin, a placement guide with a hydration inducing plug 401 and with at least one reservoir 402 in the guide's mount, and an optical probe which is coupled with the guide. The coupling agent may be delivered in a manual or in an automated fashion to the sampling site. The guide cavity or reservoir may be open to the sample surface or may have channels to the sample surface and/or sampling site. As stated above, the guide has a lock and key mechanism that interfaces a sampling site to a bioanalyzer such as near-IR based noninvasive glucose concentration analyzer.

Coupling Agent Properties

Index Matching: The coupling fluid itself may be any index of refraction matching solution. However, it is preferably near-IR inactive. That is it is preferably a chlorofluorocarbon molecule or a chlorofluorocarbon polymer. Because the chlorine in a chlorofluorocarbon is associated with toxicity, it is preferable that the coupling fluid be a fluorocarbon molecule, a fluorocarbon polymer, a fluorocompound, or a mixture of any of these. Some specific examples are FC-40, FC-70, and FC-72 available from 3M. The index of refraction of FC-72, FC-40, and FC-70 is 1.251, 1.290, and 1.303, respectively. This is intermediate between skin with a refractive index of 1.44 and air with a refractive index of 1.0 and thus, according to Fresnel, may increase the percentage of normally incident photons penetrating into the skin. In the case where a Teflon hydration inducing layer is used, the FC-compounds with an index of refraction ranging from about 1.25 to 1.31 is well matched to Teflon AC with an index of refraction of 1.29 to 1.32. The coupling fluid may alternatively serve the purpose of partially penetrating into the skin to provide better optical coupling more internalized layers of skin. For example, the fluorinert may wet the keratinocytes, displace air pockets, and generally level the rough surface.

Thermal: The reservoir(s) 402 within the guide has several thermal advantages. First, the guide material about the reservoir acts as an insulator to environmental conditions. For example, if the subject steps outside into a cold environment, there can be a delay in the cooling of the coupling fluid due to the insulator. An optional additional insulator such as a wrap or sleeve may be used in the event that the guide provides insufficient insulation. Second, the proximity of the reservoir to the skin allows for the coupling fluid to be naturally maintained at or near the skin temperature. This is advantageous as changes in the temperature of the sampling site may be detrimental to near-IR based noninvasive glucose determinations. Hence, application of cold coupling fluids to the sampling site just prior to noninvasive sampling may degrade analytical performance of a glucose analyzer by changing the sample site temperature. In the system as presented in FIGS. 4A-4B, the movement of the coupling fluid to the sampling site from the reservoir(s) 402 is along the skin surface thus maintaining the coupling fluid temperature and resulting in minimal changes to the sampling site temperature. In the embodiment as shown in FIG. 4A, for example, the Teflon hydration inducing plug 401 further insulates the coupling fluid temperature during the migration.

Mechanical: It should be appreciated that the schematic of FIG. 4 presents just one of a wide variety of mechanisms for the coupling agent to be delivered from the guide reservoir to the sampling site. Many shapes and positions of the reservoir(s) may be readily designed and many channels, tunnels, or patterns for movement of the coupling agent from the reservoir to the sampling site may be designed without altering the scope of the invention.

Optical: The intent of the photon traces in FIG. 4A is for illustrative purposed only. It is recognized that the actual optical paths traveled are far more complex with interactions to many layers and structures that are not presented beyond a schematic level. For example, the Teflon spacer may be of multiple layers, have varying density with radial position, or be shaped into optics as described above. Similarly, the skin structure and optical probe have many details and layers beyond the schematic presentation.

Delivery: The coupling fluid is directed to the sample site by at least one of: (1) gravity; (2) diffusion; (3) a guiding channel; (4) a mechanical pump; (5) manually applied pressure; and (6) an electromechanical system such as an intelligent polymer system.

Embodiments described below may use one or more of these delivery forces. The energy used by these systems may be provided by one or more of a manually applied force, an internal power supply such as a battery, an external power supply, or natural forces, such as diffusion or gravity.

These delivery systems reduce chances for contamination and insure adequate delivery of the agent to the sampling site.

One embodiment of a coupling agent cavity in a guide lock and key mechanism is indicated conceptually in FIG. 4A. A cavity or reservoir 402 in the guide may contain an optical coupling agent such as those described below. This system is pictured as a diffusion-based coupling agent delivery system; however other mechanisms for delivery may be used with this configuration. In this system, the internal reservoir of coupling fluid diffuses out to the sampling site. The coupling agent is guided through one or more channels to the optical sampling site. The channels may be in direct contact with the skin and/or may lead through the guide element to the sampling site. A barrier to direct the coupling agent toward the sampling site as opposed to away from the sampling site may be any of: (1) contact of the guide to the skin to act as a physical barrier; (2) a physical barrier on the guide such as a ridge that minimally deforms the skin to form a physical barrier around the sampling site; and (3) an adhesive on the guide that circumscribes the sampling site and couples the guide to the skin around the sampling site.

The optical coupling agent (fluid) then travels inward toward the center of the sampling site. Optionally, a hydration inducing plug such as one described above may be used. In this case, the optical coupling fluid would preferably flow and spread between the outer surface of the hydration inducing plug and the skin surface of the sampling site.

Figure 4B:
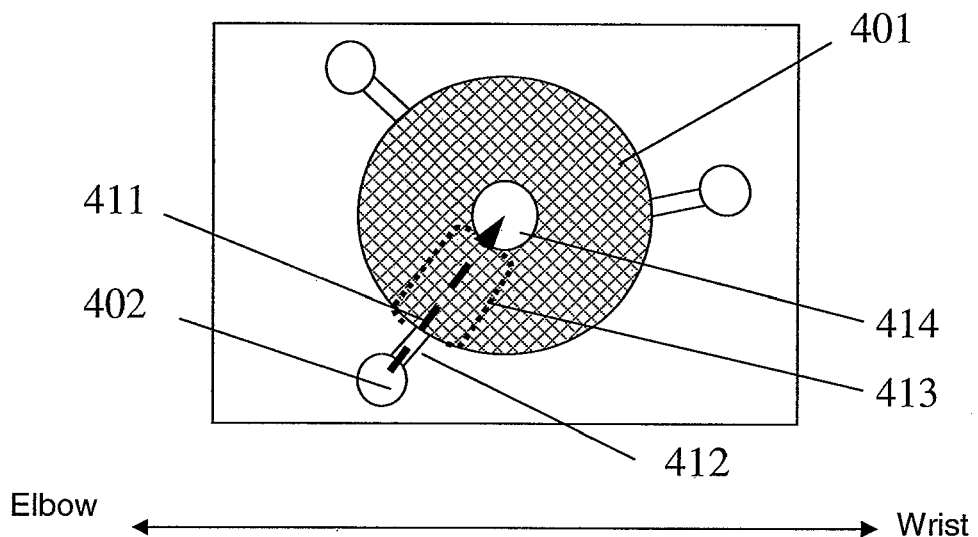
FIG. 4B is a schematic diagram showing the top view of the guide's mount with three reservoirs and the hydration inducing plug according to the invention.

In the embodiment pictured in FIG. 4A, an optional fluoropolymer hydration inducer is shown. This allows the optical coupling fluid to be maintained next to the skin surface. In the configuration as presented in FIG. 4B, three entrance channels are designed. One, two, three or many channels may be used. In this system, containment of the coupling fluid is desirable in order to keep the fluid from merely running around the sampling site. As the arrow 411 in FIG. 4B shows, moving radially inward, the optical coupling fluid flows from the reservoir 402, passing a non-optically sampled region 412, through a region 413 that may be used to introduce photons into the sampling skin, and finally to a central area 414. As described above, the hydration inducing plug may have a hole in its center, and the collection optics is fittingly coupled into the hole when the guide lock and key mechanism is coupled together. Notably, the coupling fluid reservoirs may be used without the Teflon hydration inducing plug.

Figure 4C:
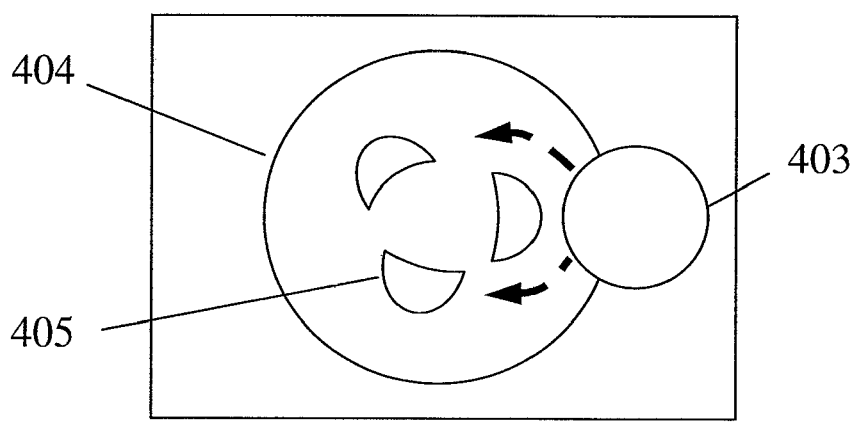
FIG. 4C is a schematic diagram showing the top view of the guide's mount with a single reservoir and the hydration inducing plug according to the invention.

Another possible configuration of such a guide with one internal reservoir or cavity for containing a coupling fluid is presented in FIG. 4C. In this configuration, the single reservoir 403 is designed within the guide's mount. This system uses mechanical force to induce movement of the coupling fluid from the reservoir 403 to the sampling site. For example, the reservoir 403 within the guide may be under any of: (1) a manual press button, wherein pressing the button forces a plunger or the like to drive the coupling fluid out of the reservoir; (2) a mechanical pump; and (3) a thin wall blister, wherein application of force by for example a finger causes the blister to deform physically pushing the coupling fluid our of the reservoir. Additional driving forces as described in this specification may be used to drive the coupling fluid. A barrier 404 may be used to contain the coupling fluid from the reservoir 403 within the guide. This barrier may be circular, oval, or a number of other simple and/or complex shapes. One or more optional barriers 405 within the contained region force the coupling fluid to enter the center sampling area from one or more directions.

In the configurations as presented in FIG. 4B and FIG. 4C, a gravity feed system or other driving mechanisms may be used. To enhance a gravity fed system, the reservoir or reservoirs are positioned within the guide based upon the sampling site location and common anatomical positions. Sample sites include any of the arm, base of thumb, back of wrist, volar or dorsal aspect of the forearm, and upper arm, head, torso, abdominal region, leg, thigh, and calf. The preferred sampling sites are the top of the forearm or the back of the wrist. For both of these anatomical sites, natural physiological positions are for the arm to hang down by ones side or to rest on an armrest. This leads to logical positioning of the coupling agent reservoir to be above (towards the elbow) the sampling site. Thus, when the arm is hanging down by the side of the subject, gravity is pulling the coupling fluid out of the reservoir nearest the elbow down towards the sampling site. Also, as the arm may rotate reservoirs may be on either side of the sampling site. Thus, with rotation of the arm, the coupling fluid may flow by gravity from one of the two side reservoirs towards the sampling site. While one or more reservoirs are possible, in the preferred arrangement three reservoirs are placed around the sampling site at roughly the points of an isosceles triangle. A single ring reservoir around the sampling site is also possible, but is not preferred as the coupling fluid may just run around the sampling site.

The guide's lock base, i.e. the unit including the mount together with the hydration inducing plug and any other accessories such as the adhesive layer(s), physical guiding component(s), coupling agent reservoir(s), and coupling fluid may be a disposable. The guide unit may be an item applied to a sampling site for the period of about one day, one waking day, or shorter period such as about two, four, or eight hours. For professional use, such as use in conjunction with a glucose tolerance test, the guide unit may be attached for a fraction of a day such as for two, four, or six hours. Alternatively, the guide unit as a whole may be an apparatus that is periodically removed from the sampling site and later replaced, perhaps with new adhesives.

The optical unit, i.e. the optical probe, coupling into the guide base may be created in a number of optical configurations. For example, fiber optics may be used to deliver light to the sample and/or to collect light from the sample. Notably, other optical configurations may be employed. For example, hollow tubes may be used for guiding the excitation and/or collected photons. In addition, photons may be traveling through air rather than through a fiber. This is particularly true for the incident photons.

People come in various dimensions in terms of physical length or width of a body part and curvature of that body part. Accordingly, guides may be used that have varying dimension, and curvatures. Guides may be supplied in large, medium, or small sizes each with a varying radius of curvature. Existing guides range from approximately 0.5 to 1.5 inches in diameter. Larger guides are readily developed. It is desirable to manufacture smaller guides as the noninvasive glucose analyzer is engineered to smaller sizes.

A number of individual elements are presented in this invention. It is important to note that many of these elements or features may be used in conjunction with one another. The invention is intended to employ at least one of: a plug, a multi-layer coupling hydration inducing plug, a coupling layer that is pressed into a non-flat sheet, a plug with a hole, an optically shaped coupling plug, a coupling fluid reservoir, and channels for diffusion or manual control of delivery of a coupling fluid.

In view of the different possible embodiments to which the principle of this invention may be applied, it should be recognized that the preferred embodiments described herein with respect to the drawings are meant to be illustrative only and should not be taken as limiting the scope of the invention. One skilled in the art will readily appreciate that other applications may be substituted for those set forth herein without departing from the spirit and scope of the invention.

Accordingly, the invention should only be limited by the Claims included below.

The invention claimed is:

1. A placement guide used for coupling of an optical probe of an optically based noninvasive glucose concentration analyzer to a sample site of a skin sample, said optical probe comprising at least one optical incident member for delivering incident photons into the sample site and an optical collection member for collecting photons emerging from the sample site, said guide comprising:
   a mount having a contact surface at one end;
   an aperture, defined by said mount, which is adapted to receive said optical probe during use, wherein an area defined by said aperture comprises the sample site; and
   a hydration inducing plug covering said aperture, wherein an outer surface of said hydration inducing plug aligns with said contact surface of said mount, said outer surface adapted to be in proximate contact with the sample site during use;
   wherein said hydration inducing plug acts as an optical interface between said optical probe and the sample site when said optical probe is coupled into said aperture, and
   wherein said hydration inducing plug has an aperture formed in its center thereof, wherein upon said optical probe being coupled with said guide, said optical collection member of said optical probe is coupled into said aperture and is adapted to have direct contact with the sample site, while said optical incident member of said optical probe is adapted to maintain direct contact with a surrounding area of said hydration inducing plug.

2. The guide of claim 1, wherein said hydration inducing plug comprises a hydrophobic material.

3. The guide of claim 1, wherein said hydration inducing plug comprises a fluoropolymer material.

4. The guide of claim 1, wherein said hydration inducing plug comprises multiple layers.

5. The guide of claim 4, wherein each of said layers comprises its own physical properties.

6. The guide of claim 1, wherein said mount comprises a plurality of channels for delivery of a coupling fluid, each of said channels being connected to a coupling fluid reservoir, said coupling fluid spreading between the outer surface of said hydration inducing plug and the skin surface of the sample site during use.

7. The guide of claim 1, wherein said hydration inducing plug comprises a hydrophobic near-IR transmissive material from 1100 to 1900 nm.

8. The guide of claim 1, wherein said hydration inducing plug comprises a material index of refraction matched to said contact surface of said mount.

* * * * *